(12) United States Patent
Chakradhara et al.

(10) Patent No.: US 6,844,364 B2
(45) Date of Patent: Jan. 18, 2005

(54) STABILIZATION OF RETINOID COMPOUNDS

(75) Inventors: Rao S. Chakradhara, Hillsborough, NJ (US); Stephen J. Wisniewski, Doylestown, PA (US); Fa Zhang, Pennington, NJ (US); Jue-Chen Liu, Belle Mead, NJ (US); Julia Kim, Basking Ridge, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 29 days.

(21) Appl. No.: 10/052,316

(22) Filed: Jan. 18, 2002

(65) Prior Publication Data

US 2003/0032659 A1 Feb. 13, 2003

Related U.S. Application Data

(60) Provisional application No. 60/262,687, filed on Jan. 19, 2001.

(51) Int. Cl.$^7$ ............................. A61K 31/20; A61K 9/14
(52) U.S. Cl. ......................... 514/559; 514/947; 424/489
(58) Field of Search ................................. 514/559, 947, 514/725; 424/489, 401, 45

(56) References Cited

U.S. PATENT DOCUMENTS

| | | | | |
|---|---|---|---|---|
| 4,247,547 A | * | 1/1981 | Marks | 514/179 |
| 4,497,794 A | * | 2/1985 | Klein et al. | 514/29 |
| 4,720,353 A | * | 1/1988 | Bell | 516/23 |
| 4,826,828 A | * | 5/1989 | Wilmott et al. | 514/63 |
| 5,037,829 A | * | 8/1991 | Freyne et al. | 514/266.23 |
| 5,726,191 A | | 3/1998 | Klaus et al. | |
| 5,958,956 A | | 9/1999 | Klaus et al. | |
| 6,193,956 B1 | * | 2/2001 | Liu et al. | 424/45 |
| 6,200,597 B1 | * | 3/2001 | Mehta et al. | 424/450 |
| 6,461,622 B2 | * | 10/2002 | Liu et al. | 424/401 |

OTHER PUBLICATIONS

Product overview of Benzamycin® Topical Gel, Physicians' Desk Reference, 1997 51$^{st}$ Edition, Medical Economics Company, Inc,, Monvtvale, NJ, pp. 919–920.

Immungo AG, "TISSEEL VH Kit", U.S. Food and Drug Administration, 'Online! May 1998, pp. 1–4, XP002211954 retrieved from internet: url:http:www.fda.gov/cber/label/fiboih0501981ab.pdf.

* cited by examiner

Primary Examiner—Vickie Kim

(57) ABSTRACT

The present invention relates to a method of administering a compound of Formula I:

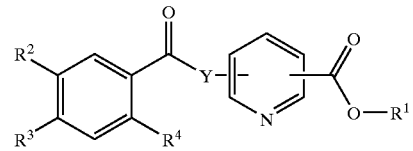

Formula I wherein
  $R^1$ is hydrogen or $C_{1-6}$-alkyl;
  $R^2$ is $C_{1-6}$-alkyl or adamantyl;
  $R^3$ is $C_{1-6}$-alkyl or hydroxy; or
  $R^2$ and $R^3$ taken together are —$(CR^6R^7)_n$—;
  $R^4$ is $C_{2-8}$-alkyl, $C_{2-8}$-alkenyl, $C_{2-8}$-alkynyl, —$OCH_2R^5$ or $C_{2-8}$-alkanoyl, or hydrogen when $R^3$ is hydroxy;
  $R^5$ is $C_{1-6}$-alkyl, $C_{2-6}$-alkenyl or $C_{2-6}$-alkynyl;
  $R^6$ and $R^7$ are hydrogen or $C_{1-6}$-alkyl;
  Y is oxygen or sulfur; and
  n is 3, 4, or 5,
or a pharmaceutically acceptable salts of carboxylic acid of formula I,
wherein said method comprises the step of admixing said compound in solid form with a topical carrier to form a topical formulation within seven days prior to first topical administration of said compound.

20 Claims, No Drawings

STABILIZATION OF RETINOID COMPOUNDS

CROSS-REFERENCE

This application claims priority from provisional application Ser. No. 60/262,687 filed on Jan. 19, 2001.

FIELD OF THE INVENTION

The present invention relates to the topical delivery of retinoid compounds.

BACKGROUND OF THE INVENTION

Retinoic acid is a retinoid sold both for the topical treatment of acne (Retin-A®, Ortho Dermatological, Skillman, N.J.) and for the topical treatment of fine wrinkles, mottled hyperpigmentation, and tactile roughness of facial skin (Renova®, Ortho Dermatological). The compound is formulated into a variety of topical gels, creams, and solutions.

U.S. Pat. No. 5,726,191 recently reported a new class of retinoids. According to the '191 Patent, these compounds can be topically administered in ointments, tinctures, creams, solutions, lotions, sprays, and suspensions. Applicants, however, have found that while members of this class of compounds were very potent in binding to the retinoid receptor, they are chemically unstable in topical formulations.

In fact, applicants tested Compound I, a compound from this class, in a vast array of topical liquid or semisolid pharmaceutical formulations. None of these formulations, however, were capable of sufficiently stabilizing the compound when stored at room temperature (between 20 to 30° C.), thus, inhibiting the ability to market the compound in a topical formulation.

The present invention relates to stabilizing this new class of retinoids in a manner suitable for topical administration.

SUMMARY OF THE INVENTION

In one aspect, the invention features a method of administering a compound of Formula I (defined herein), wherein the method includes the step of admixing the compound in solid form with a topical carrier to form a topical formulation within seven days prior to first topical administration of the compound.

In another aspect, the invention features a kit comprising two chambers, wherein the first chamber contains a compound in solid form and the second chamber contains a topical carrier in an amount capable of dissolving or dispersing said compound where the compound is of Formula I.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

In one aspect, the present invention relates to a method of administering a compound of Formula I

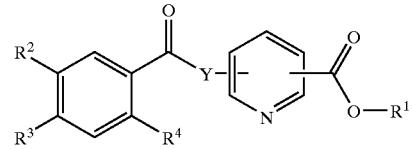

Formula I wherein $R^1$ is hydrogen or $C_{1-6}$-alkyl;

$R^2$ is $C_{1-6}$-alkyl or adamantyl;

$R^3$ is $C_{1-6}$-alkyl or hydroxy; or $R^2$ and $R^3$ taken together are —$(CR^6R^7)_n$—;

$R^4$ is $C_{2-8}$-alkyl, $C_{2-8}$-alkenyl, $C_{2-8}$-alkynyl, —$OCH_2R^5$ or $C_{2-8}$-alkanoy, or hydrogen when $R^3$ is hydroxy;

$R^5$ is $C_{1-6}$-alkyl, $C_{2-6}$-alkenyl or $C_{2-6}$-alkynyl;

$R^6$ and $R^7$ are hydrogen or $C_{1-6}$-alkyl;

Y is oxygen or sulfur; and n is 3, 4, or 5, or a pharmaceutically acceptable salts of the carboxylic acid of formula I.

The notations "$C_{1-6}$", "$C_{2-6}$", and "$C_{2-8}$" used herein stand for groups with from 1 to 6, from 2 to 6 and from 2 to 8 carbon atoms, respectively. Alkyl residues can be straight-chain or branched. The alkyl residues of $R^1$ may be straight-chain such as methyl, ethyl, propyl, butyl, pentyl and hexyl. Alkyl residues of $R^2$ and $R^3$ may be branched alkyl residues such as tert-butyl. Alkyl residues of $R^4$ and $R^5$ may be straight-chain such as ethyl, propyl, butyl, pentyl, and hexyl. Examples of alkenyl residues are straight-chain alkenyl residues such as vinyl, 1- and 2-propenyl, and 2-butenyl. Ethynyl, 1- and 2-propynyl and 1- and 2-butynyl are examples of alkynyl residues. Examples of $C_{2-8}$-alkanoyl residues are straight-chain alkanoyl residues such as acetyl, propionyl, butyryl, pentanoyl, hexanoyl, heptanoyl and octanoyl.

In one embodiment of the invention the pyridine-carboxylic acid residue in the compounds of Formula I is a nicotinic acid residue, that is, when $R^1$ is hydrogen (e.g., a nicotinic acid residue linked in the 5- or 6-position). In one embodiment, $R^2$ and $R^3$ taken together are —$(CR^6R^7)_n$—. In a further embodiment, $R^2$ and $R^3$ taken together are —$C(CH_3)_2CH_2CH_2C(CH_3)_2$—, —$C(CH_3)_2(CH_3)_2$—, or —$C(CH_3)_2(CH_2)_4$—. In one embodiment, Y is oxygen. In one embodiment, $R^4$ is $C_{2-8}$-alkyl. In one embodiment, $R^1$ is hydrogen.

Examples of compounds of Formula I are the following:

Compund I

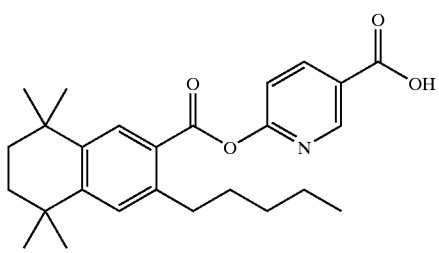

Compound II

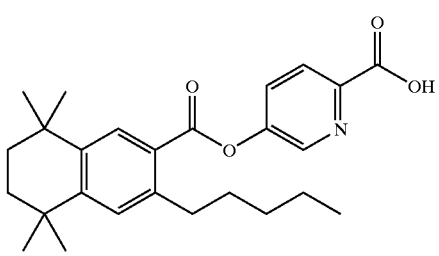

Compound III

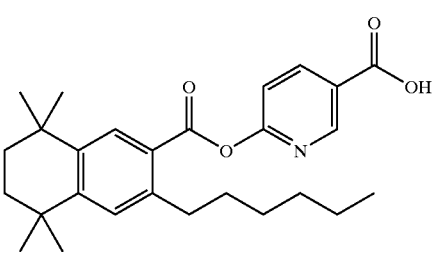

Other examples of compounds of formula I are:
6-(3-hexyl-5,5-dimethyl-6,7,8,9-tetrahydro-5H-benzocyclohepten-2-yl-carbonyloxy)-nicotinic acid,
6-(3-hex-1-enyl-5,5,8,8-tetramethyl-5,6,7,8-tetrahydro-naphthalen-2-yl-carbonyloxy)-nicotinic acid,
6-(6-hexyl-3,3-dimethyl-indan-5-yl-carbonyloxy)-nicotinic acid,
6-(3-butoxy-5,5,8,8-tetramethyl-5,6,7,8-tetrahydro-naphthalen-2-yl-carbonyloxy)-nicotinic acid,
6-(3-adamantan-1-yl-4-hydroxy-benzoyloxy)-nicotinic acid,
6-(3-hexanoyl-5,5,8,8-tetramethyl-5,6,7,8-tetrahydro-naphthalen-2-yl-carbonyloxy)-nicotinic acid, and
6-(3-hexyl-5,5,8,8-tetramethyl-5,6,7,8-tetrahydro-naphthalen-2-yl-carbonylsulphanyl)-nicotinic acid.

Methods of manufacturing compounds of the present invention are set forth in U.S. Pat. No. 5,726,191.

In one embodiment, the topical carrier substantially dissolves said compound (e.g., dissolves at least 90% of the compound). In one embodiment, the topical carrier suspends the compound. In one embodiment, the composition comprises about 0.001% to about 1%, by weight, of the compound (e.g., about 0.01% to about 0.1%, by weight).

In one embodiment, the method includes admixing a unit dose of the compound (e.g., an amount of the compound sufficient for a single application of the compound). In a further embodiment, the topical carrier comprises an alcohol. Examples of such alcohols include, but are not limited to, the group consisting of ethanol, isopropyl alcohol, and propylene glycol. In one embodiment, the topical carrier further includes an gelling agent. In one-embodiment, the gelling agent is an oil-soluble gelling agent. Suitable gelling agents for oils (such as mineral oil) include, but are not limited to, hydrogenated butylene/ethylene/styrene copolymer and hydrogenated ethylene/propylene/styrene copolymer. Such gels typically comprises between about 0.1% and 5%, by weight, of such gelling agents.

In another embodiment, the method includes admixing multiple unit dosages of the compound. In a further embodiment, the topical carrier comprises a member selected from the group consisting of diisopropyl adipate, diisopropyl sebacate, diisocetyl adipate, triacetin, caprylic/capric triglyceride, and isopropyl myristate. In a further embodiment, the method further includes the step of refrigerating the resulting formulation during the course of administration of the multiple unit dosages.

In one embodiment, the method further comprises admixing the formulation containing the compound with a cream (e.g., a water-in-oil emulsion or oil-in-water emulsion) or a gel (e.g., an aqueous, petrolatum, or silicone gel).

In another aspect, the invention features a kit comprising two chambers, wherein the first chamber contains the compound in solid form and the second chamber contains a topical carrier in an amount capable of dissolving or dispersing said compound where the compound is of Formula I.

In one embodiment, the topical carrier is in an amount capable of substantially dissolving the compound. In one embodiment, the topical carrier is in an amount capable of suspending the compound.

In one embodiment, the first chamber contains a unit dose of the compound. In a further embodiment, the topical carrier contains an alcohol. In a further embodiment, the second chamber further contains a gelling agent.

In one embodiment, the first chamber contains multiple unit dosages of the compound. In a further embodiment, the solvent is selected from the group consisting of diisopropyl adipate, diisopropyl sebacate, diisocetyl adipate, triacetin, caprylic/capric triglyceride, and isopropyl myristate. In a further embodiment, the kit further includes a label instructing the user to refrigerate the compound following dissolution.

In one embodiment, the kit further comprises a third chamber containing a cream (e.g., a water-in-oil emulsion or oil-in-water emulsion) or a gel (e.g., an aqueous, petrolatum, or silicone gel).

In one embodiment, the first chamber and second chamber are separate containers (e.g., vials). The contents of one container may then be added and admixed with the contents of the other container (e.g., the compound may be removed from its container and added and admixed with the topical carrier in its container). In a further embodiment, the resulting mixture is administered by using a wipe applicator that may or may not be stored within the other container. Examples of such administration is well known in the art, e.g., Benzamycin® topical gel.

In another embodiment, the two chambers are within the same container, but are separated by a wall that is breakable upon the application of force. Examples of two chamber packages for delivery of unit dosages are well known in the art and are available from supplier such as Klocke Verpackungs GmbH (Weingarten, Germany). In a further embodiment, the resulting mixture is administered by using a wipe applicator that may or may not be stored within the container.

Unit dosages may also be administered using applicator stick wherein the topical carrier is stored within the shaft of the applicator and separated from the applicator end of stick by a breakable wall. The compound of Formula 1 is contained within the applicator end of the stick (e.g., a foam or fabric tip). Upon rupturing the breakable wall, the topical carrier enters the foam head and dissolves/suspends the compound. Examples of such applicators are well known in the art, e.g., Betadine PrepStick™ applicator (Purdue Frederick, Norwalk, Conn.).

The compounds of the present invention are useful in the treatment or prevention of skin disorders such as acne, psoriasis, photo-damage, environmental damage, intrinsic age damage, wrinkles, tumors (e.g., melanomas), hyperpigmentation, and skin roughness. The compounds of the present invention may also be used for the promotion of wound healing. Other uses of the present invention are set forth in U.S. Pat. No. 5,726,191.

As discussed above, compounds of the present invention were found to be chemically unstable once formulated into a topical carrier. What is meant by a topical carrier is a liquid or semi-solid formulation capable of being applied topically to the skin. Examples of topical carriers include, but are not limited to, ointments, sprays, creams, lotions (e. g., solutions, suspensions and emulsions), or gels. The topical carrier is preferably anhydrous.

Thus, in order to ensure stability of such compounds, they must be stored in solid form, and then reformulated into a topical carrier proximate to the time of first application (e.g., within seven days prior to the first topical administration of said compound). In one embodiment, the compound is reformulated within forty-eight (48) hours prior to first topical administration of said compound. In one embodiment, the compound is mixed by a doctor, pharmacist, or by the end user.

The following is a description of the manufacture of various topical formulations of the present invention. Other formulations of the invention can be prepared in an analogous manner by a person of ordinary skill in the art.

EXAMPLE 1

The stability of Compound I was tested in the following twenty-eight different topical formulations, set forth in Table 1. Finsolv® TN is a C12–15 alkyl benzoate from Fintex, Inc. (Elmwood Park, N.J.) Miglyol® 812 from Huls AG (Marl, Germany) and Neobee® 1053 from Stepan Company (Northfield, Ill.) are each a caprylic/capric triglyceride.

TABLE 1

| Formulation No. | Carrier | Volume % |
| --- | --- | --- |
| Formulation 1 | Diisopropyl sebacate | 100 |
| Formulation 2 | Diisopropyl sebacate | 60 |
|  | Cyclomethicone | 40 |
| Formulation 3 | Miglyol ® 812 | 100 |
| Formulation 4 | Isopropyl laurate | 100 |
| Formulation 5 | Diisopropyl sebacate | 50 |
|  | Isopropyl laurate | 50 |
| Formulation 6 | Diisopropyl adipate | 50 |
|  | Cyclomethicone | 50 |
| Formulation 7 | Diisopropyl adipate | 100 |
| Formulation 8 | Diisopropyl adipate | 50 |
|  | Isopropyl laurate | 50 |
| Formulation 9 | Propylene glycol | 100 |
| Formulation 10 | PEG 400 | 100 |
| Formulation 11 | Propylene carbonate | 100 |
| Formulation 12 | Dimethyl isosorbide | 100 |
| Formulation 13 | Miglyol ® 812 | 100 |
| Formulation 14 | Finsolv ® TN | 100 |
| Formulation 15 | Glycerin | 100 |
| Formulation 16 | Isopropyl myristate | 100 |
| Formulation 17 | Cyclomethicone | 100 |

TABLE 1-continued

| Formulation No. | Carrier | Volume % |
| --- | --- | --- |
| Formulation 18 | Dimethicone | 100 |
| Formulation 19 | Mineral oil | 100 |
| Formulation 20 | Sunflower oil | 100 |
| Formulation 21 | Soybean oil | 100 |
| Formulation 22 | Neobee ® 1053 | 100 |
| Formulation 23 | Sesame oil | 100 |
| Formulation 24 | Butyl Acetate | 100 |
| Formulation 25 | Isopropanol | 100 |
| Formulation 26 | PEG 400 | 30 |
|  | Ethanol | 70 |
| Formulation 27 | Triacetin | 100 |
| Formulation 28 | Tributyrin | 100 |

The general procedure to prepare the above formulations is as follows. A 500 mg of Compound 1 was weighed and transferred into an 800 ml glass beaker containing 500 g of one of the above carriers. The formulation was then stirred with a paddle mixer (stirrer type RZR50 from Caframo in Wiarton, Ontario, Canada) at 100 RPM setting until the compound was completely dissolved/dispersed in the carrier.

About 20 g each of the resulting formulations were then packed into 24 clear glass scintillation vials of 20 ml volume (Wheaton Disposable Scintillation Vials from Wheaton Scientific in Milleville, N.J.) and labeled. Groups of eight of such vials were then stored at 4° C., RT (22° C.) and/or 40° C. for stability studies.

The samples of the formulations at each of the above three temperatures were then periodically analyzed for the chemical stability of Compound 1. The compound was assayed using high performance liquid chromatographic (HPLC) system. The results of this analysis is set forth in Table 2 setting forth the amount of Compound 1 remaining in the formulation following a certain number of days at specified temperatures. Chemical degradation of Compound 1 was seen in all of the formulations stored at 22° C. and/or 40° C., thus, demonstrating a need to make the formulation proximate to the time of administration and/or refrigerate the formulation after it is made.

TABLE 2

| | | % Remaining | | |
| --- | --- | --- | --- | --- |
| Formulation No. | Days | 4° C. | 22° C. | 40° C. |
| Formulation 1 | 84 | 102 | 89 | 64 |
| Formulation 2 | 84 | 101 | 90 | 68 |
| Formulation 3 | 56 | 100 | 93 | 60 |
| Formulation 4 | 56 | 100 | 97 | 87 |
| Formulation 5 | 56 | 100 | 96 | 80 |
| Formulation 6 | 90 | 87 | 84 | 63 |
| Formulation 7 | 90 | 87 | 80 | 57 |
| Formulation 8 | 90 | 100 | 93 | 69 |
| Formulation 9 | 36 | 82.39 | — | 0.71 |
| Formulation 10 | 36 | 93.56 | — | 0.71 |
| Formulation 11 | 70 | 100.77 | — | 40.18 |
| Formulation 12 | 18 | 96.84 | — | 65.36 |
| Formulation 13 | 70 | 93.46 | — | 49.09 |
| Formulation 14 | 36 | 100.48 | — | 2.23 |
| Formulation 15 | 29 | 97.44 | — | 84.09 |
| Formulation 16 | 22 | 95.43 | — | 86.18 |
| Formulation 17 | 85 | 100 | — | 83 |
| Formulation 18 | 30 | 98.16 | — | 76.18 |
| Formulation 19 | 70 | 104.83 | — | 84.83 |
| Formulation 20 | 70 | 102.20 | — | 51.83 |
| Formulation 21 | 22 | 101.34 | — | 83.82 |
| Formulation 22 | 21 | 100 | 97.38 | 88.62 |

TABLE 2-continued

| Formulation No. | Days | % Remaining | | |
|---|---|---|---|---|
| | | 4° C. | 22° C. | 40° C. |
| Formulation 23 | 23 | 102.66 | — | 86.77 |
| Formulation 24 | 34 | 100 | — | 55.48 |
| Formulation 25 | 18 | 100 | 80.79 | 5.96 |
| Formulation 26 | 13 | 100 | 86.74 | 9.13 |
| Formulation 27 | 23 | 100 | 96.41 | 93.81 |
| Formulation 28 | 22 | 100 | 97.49 | 86.08 |

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of enhancing the stability during administeration of multiple unit dosages of a compound of Formula I:

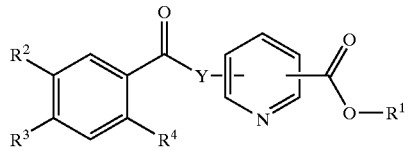

Formula I wherein $R^1$ is hydrogen or $C_{1-6}$-alkyl;

$R^2$ is $C_{1-6}$-alkyl or adamantyl;

$R^3$ is $C_{1-6}$-alkyl or hydroxy; or $R^2$ and $R^3$ taken together are —$(CR^6 R^7)_n$—;

$R^4$ is $C_{2-8}$-alkyl, $C_{2-8}$-alkenyl, $C_{2-8}$-alkynyl, —$OCH_2R^5$ or $C_{2-8}$-alkanoyl, or hydrogen when $R^3$ is hydroxy;

$R^5$ is $C_{1-6}$-alkyl, $C_{2-6}$-alkenyl or $C_{2-6}$-alkynyl;

$R^6$ and $R^7$ are hydrogen or $C_{1-6}$-alkyl;

Y is oxygen or sulfur; and n is 3, 4, or 5, or a pharmaceutically acceptable salts of carboxylic acid of formula I, wherein said method comprises the step of admixing multiple unit dosages of said compound in solid form with a topical carrier to form a topical formulation within forty-eight hours prior to first topical administration of said formulation, and refrigerating said formulation during the course of administration of said multiple unit dosages.

2. A method of claim 1, wherein said topical carrier substantially dissolves said compound.

3. A method of claim 1, wherein said topical carrier suspends said compound.

4. A method of claim 1, wherein said topical carrier further comprises a gelling agent.

5. A method of claim 2, wherein said topical carrier comprises a member selected from the group consisting of diisopropyl adipate, diisopropyl sebacate, diisocetyl adipate, triacetin, caprylic/capric triglyceride, and isopropyl myristate.

6. A method of claim 1, wherein said formulation comprises about 0.01% to about 0.1%, by weight, of said compound.

7. A method of claim 5, wherein said method further comprises admixing said formulation comprising said compound with a cream or a gel.

8. A method of claim 1, wherein said method further comprises admixing said formulation comprising said compound with a cream or a gel.

9. A method of claim 1, wherein said compound is

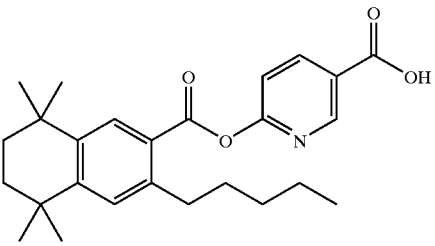

or a pharmaceutically acceptable salt thereof.

10. A method of claim 2, wherein said compound is

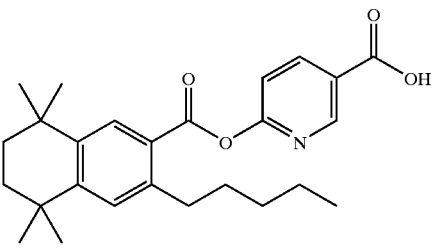

or a pharmaceutically acceptable salt thereof.

11. A method of claim 3, wherein said compound is

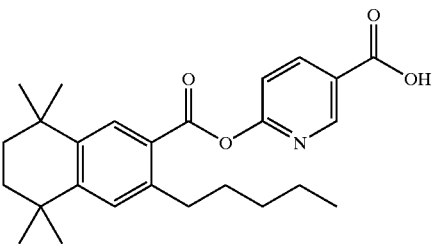

or a pharmaceutically acceptable salt thereof.

12. A method of claim 4, wherein said compound is

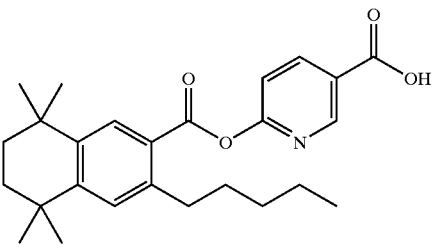

or a pharmaceutically acceptable salt thereof.

13. A method of claim 5, wherein said compound is

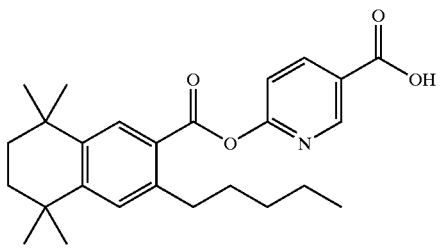

or a pharmaceutically acceptable salt thereof.

14. A method of claim 6, wherein said compound is

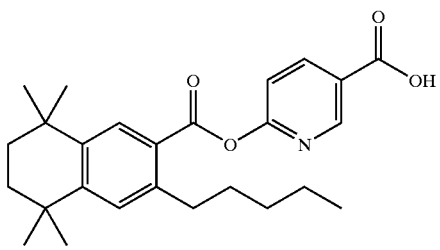

or a pharmaceutically acceptable salt thereof.

15. A method of claim 7, wherein said compound is

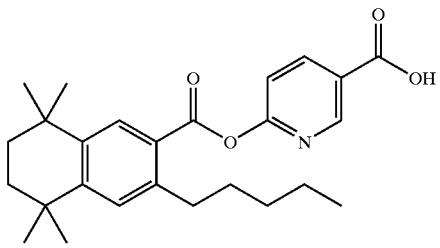

or a pharmaceutically acceptable salt thereof.

16. A method of claim 8, wherein said compound is

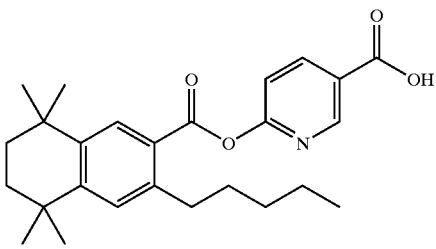

or a pharmaceutically acceptable salt thereof.

17. A method of claim 1, wherein said topical carrier comprises a member selected from the group consisting of diisopropyl adipate, diisopropyl sebacate, diisocetyl adipate, triacetin, caprylic/capric triglyceride, and isopropyl myristate.

18. A method of claim 17, wherein said formulation comprises about 0.01% to about 0.1%, by weight, of said compound.

19. A method of claim 17, wherein said compound is

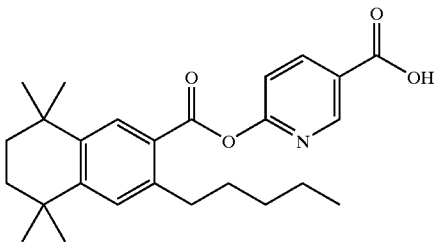

or a pharmaceutically acceptable salt thereof.

20. A method of claim 18, wherein said compound is

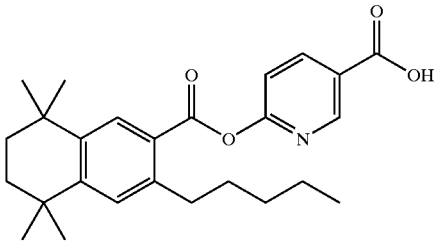

or a pharmaceutically acceptable salt thereof.

* * * * *